United States Patent [19]

Uesugi et al.

[11] 4,290,849
[45] Sep. 22, 1981

[54] NUCLEAR REACTOR

[75] Inventors: Nobuo Uesugi, Yokohama; Tatsuo Miyazawa, Higashi; Mituaki Furudate; Keiichi Sasaki, both of Yokohama; Hiroji Mizuguchi, Yokosuka, all of Japan

[73] Assignee: Tokyo Shibaura Denki Kabushiki Kaisha, Kawasaki, Japan

[21] Appl. No.: 953,274

[22] Filed: Oct. 20, 1978

[30] Foreign Application Priority Data

Oct. 26, 1977 [JP] Japan .............................. 52-127578

[51] Int. Cl.$^3$ ............................................. G21C 17/00
[52] U.S. Cl. ................................... 176/19 R; 367/151
[58] Field of Search ...................... 176/14 R; 367/151

[56] References Cited

U.S. PATENT DOCUMENTS

| 3,237,150 | 2/1966 | Beck et al. | 176/19 R |
| 3,303,457 | 2/1967 | Akesson | 176/19 R |
| 3,325,779 | 6/1967 | Supernaw et al. | 367/151 |
| 3,604,529 | 9/1971 | Fothergill | 367/151 |
| 3,656,074 | 4/1972 | Bevilacqua et al. | 176/19 R |
| 4,008,455 | 2/1977 | Pedersen | 176/19 R |
| 4,050,056 | 9/1977 | Massa | 367/151 |

FOREIGN PATENT DOCUMENTS

| 51-14597 | 2/1976 | Japan | 176/19 R |
| 1461944 | 1/1977 | United Kingdom | 176/19 R |

OTHER PUBLICATIONS

A Contemporary View of Elementary Physics (1968), Borowitz et al., p. 518.
Conf-760503-P-2, (5/3-6/76), Champion, Penn Lions et al., pp. 755-761.

Primary Examiner—S. A. Cangialosi
Attorney, Agent, or Firm—Oblon, Fisher, Spivak, McClelland & Maier

[57] ABSTRACT

A nuclear reactor comprising a reactor vessel, a core housed in the reactor vessel, an ultrasonic transducer mounted in the vicinity of the upper end of the core for emitting and receiving an ultrasonic wave pulse signal propagating above the core, means for rotating the transducer by a prescribed angle to scan horizontally the ultrasonic wave emitted from the transducer, a plurality of reflective means mounted in the vicinity of the upper end of the core in a manner to face the transducer for reflecting the ultrasonic wave signal emitted from the transducer, means for energizing the transducer, and means for displaying the ultrasonic wave signal reflected by the reflective members and received by the transducer in synchronism with the wave scanning motion of the transducer, wherein each reflective member comprises reflective surfaces each capable of reflecting the incident ultrasonic wave signal in a direction parallel with the incident direction and is mounted such that the distances of the reflective surfaces from the transducer are different enough from each other to prevent interference among the reflected ultrasonic wave signals.

7 Claims, 8 Drawing Figures $\theta > \sin^{-1}\dfrac{\tau c}{2a}$ $\Delta \ell > c\tau$

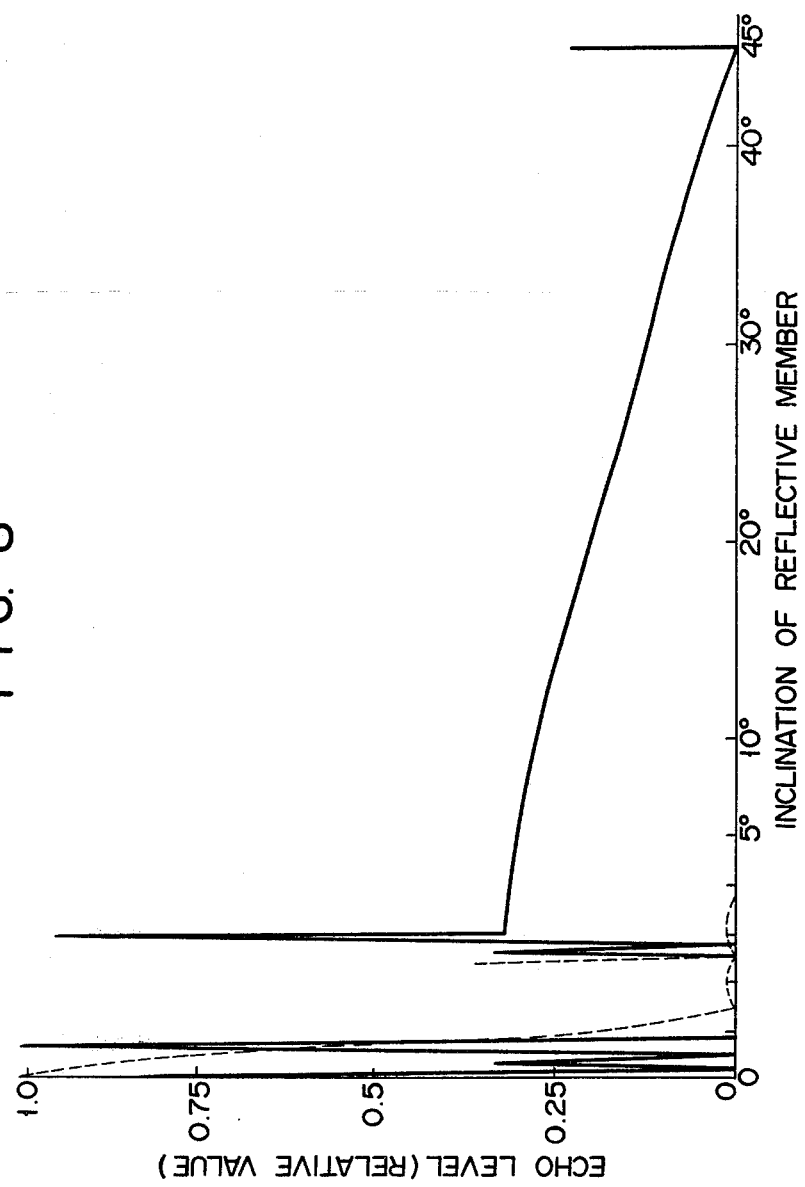

NUCLEAR REACTOR

BACKGROUND OF THE INVENTION

This invention relates to a nuclear reactor constructured to be capable of rapidly detecting an abnormalty of a core, particularly, an abnormality in the location of a fuel assembly.

A conventional nuclear reactor, for example a fast breeder, comprises a reactor 1, a core 3 formed by erecting a fuel assembly in the reactor vessel 1, an upper mechanism 4 mounted about the core 3 in a manner to face the core 3, and a rotatable plug 2 closing the upper opening of the reactor vessel 1, as shown in FIG. 1. A coolant 9 consisting of liquid sodium enters the reactor vessel through a lower inlet port (a) and flows out of the reactor vessel through an upper outlet port (b). As shown in the drawing, an ultrasonic transducer 7 and a reflective member 6, which collectively serve to detect the location and condition of a fuel assembly 5, are provided inside the reactor vessel 1 in a manner to face each other. It is seen that the transducer 7 and reflective member 6 are located to be suitable for inspection of the region between the upper mechanism 4 and the core 3. The ultrasonic transducer 7 is connected to a driving member 8 through a cable (c).

As mentioned above, the ultrasonic transducer 7 and the reflective member 6 collectively serve to detect the conditions of the fuel assembly 5. Specifically, the upper mechanism 4 is kept joined to the core 3 via a control bar or plate during operation of the nuclear reactor. Thus, for replacing the fuel assembly, it is necessary to move the upper mechanism 4 after it is detached from the core 3. It is very important to confirm the mechanical detachment of the upper mechanism 4 from the core 3 before moving the upper mechanism 4, because the fuel assembly mounted to the core 3 is sometimes caused to float so as to reach the upper mechanism 4 by thermal deformation or by the coolant 9 during operation of the nuclear reactor. Naturally, it is very dangerous to move the upper mechanism 4 when it is not sufficiently detached from the core 3. The ultrasonic transducer 7 and the reflective member 6 are used for confirming whether the upper mechanism 4 has been completely detached from the core 3. This method utilizes the ultrasonic wave generated from and received by the ultrasonic transducer 7 and comprises two types of operation.

In one type of operation, the ultrasonic transducer 7 alone is used for detecting the presence of obstacles such as the fuel assembly and control bar between the upper mechanism 4 and the core 3. Namely, the ultrasonic wave generated from the ultrasonic transducer 7 is reflected by such as obstacle, if present, and the reflective wave, or the echo, is received by the ultrasonic transducer 7. In this case, however, the detection accuracy is markedly influenced by the shape of the obstacle. For example, the fuel assembly 5 is a column hexagonal in cross section. Thus, the ultrasonic wave hitting the fuel assembly 5 is reflected in many directions, resulting in that the echo is very unlikely to return to the ultrasonic transducer 7. Further, it possibly happens that the floating fuel assembly is inclined with respect to the propagation direction of the ultrasonic wave as shown in FIG. 1. In this case, the echo travels in the direction shown by "X", resulting in failure to detect the presence of the inclined fuel assembly.

The other type of operation utilizes the reflective member 6 together with the ultrasonic transducer 7. Namely, the ultrasonic wave generated from the ultrasonic transducer 7 is reflected by the reflective member 6 to return to the transducer 7. If there is an obstacle in the passageway of the ultrasonic wave, the echo from the reflective member 6 fails to reach the transducer 7, thereby detecting the presence of the obstacle. Unlike the operation utilizing the transducer 7 alone, this type of operation relies on the absence of the echo received by the ultrasonic transducer. It follows that the presence of an obstacle can be detected regardless of the shape or inclination of the obstacle.

However, the operation involving the reflective member 6 necessitates an extremely high accuracy in mounting the reflective member. It is important to note that the reflective member should reflect the ultrasonic wave to return to the transducer. To achieve the object, it is customary to use a reflective member having the reflective surface curved to form an arc of a circle. Namely, distances of any optional points of the reflective surface from the transducer should be the same. Further, the reflective member must be mounted very accurately to permit the reflective wave to return to the ultrasonic transducer. What should also be considered is thermal deformation of the reflective member. If the reflective member fails to be positioned accurately either by inaccuracy in the mounting step or by thermal deformation, the echo fails to return to the transducer. Naturally, it is impossible to detect the presence of an obstacle in this case. Under the circumstances, it is required that the reflective member be mounted very accurately and, in addition, be adjusted very accurately when thermally deformed. It is naturally desired to alleviate the severity of the demands.

SUMMARY OF THE INVENTION

An object of this invention is to provide a nuclear reactor permitting an abnormality in the location of a fuel assembly to be detected with a sufficiently high accuracy even if a reflective member constituting a part of the detection system has been deviated from the due position.

According to this invention, there is provided a nuclear reactor comprising a reactor vessel, a core housed in the reactor vessel, an ultrasonic transducer mounted in the vicinity of the upper end of the core for generating and receiving the ultrasonic wave pulse signal propagating above the core, means for rotating the transducer by a prescribed angle to scan horizontally the ultrasonic wave emitted from the transducer, a plurality of reflective members mounted in the vicinity of the upper end of the core in a manner to face the transducer for reflecting the ultrasonic wave signal emitted from the transducer, means for energizing the transducer, and means for displaying the ultrasonic wave signal reflected by the reflective members and received by the transducer in synchronism with the wave scanning motion of the transducer, wherein each reflective member comprises reflective surfaces each capable of reflecting the incident ultrasonic wave signal in a direction parallel with the incident direction and is mounted such that the distances of the reflective surfaces from the transducer are different enough from each other to prevent interference among the reflective wave signals.

BRIEF DESCRIPTION OF THE DRAWING

FIG. 8 is a graph showing the relationship between the inclination of reflective member and the echo level for both cases of the present invention and the prior art.

DESCRIPTION OF THE PREFERRED EMBODIMENT

Figure 7:
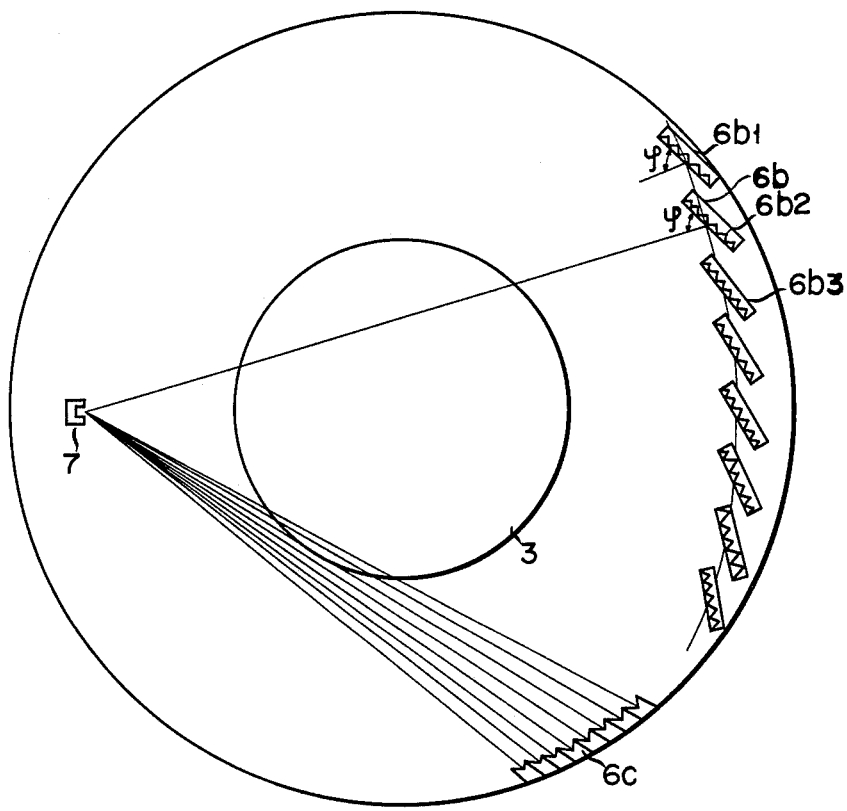
FIG. 7 is a schematic cross sectional view of a nuclear reactor according to this invention, which corresponds to the cross section along the line VII—VII of FIG. 1.

As shown in FIG. 7, the nuclear reactor according to this invention comprises a plurality of reflective members $6b$, $6b_1$, etc. serving to reflect the ultrasonic wave signal emitted from a transducer. Incidentally, FIG. 7 is a schematic cross sectional view of a nuclear reactor according to this invention, which corresponds to the cross section along the line VII—VII of FIG. 1 as mentioned previously.

Figure 2:
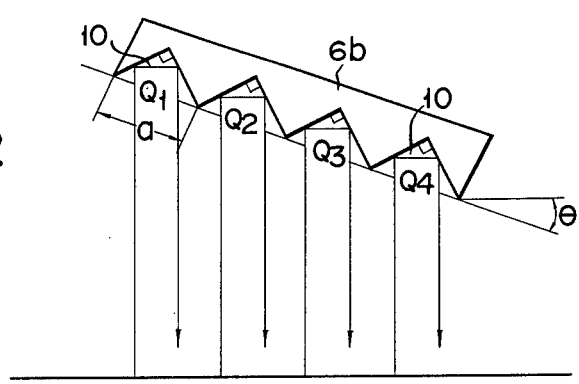
FIG. 2 is a schematic diagram used for explaining the function of a reflective member according to one embodiment of this invention.
Figure 3:
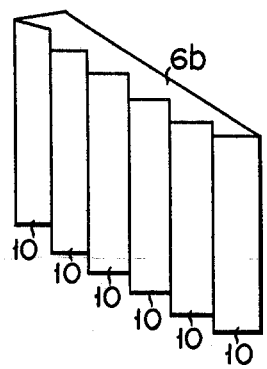
FIG. 3 is a perspective view of the reflective member shown in FIG. 2.

It is important to note that the reflective member $6b$ is provided with a plurality of grooves 10 as shown in FIGS. 2 and 3. Each groove 10 is of a particular shape. Namely, the two walls defining the groove 10 cross at right angles.

Figure 1:
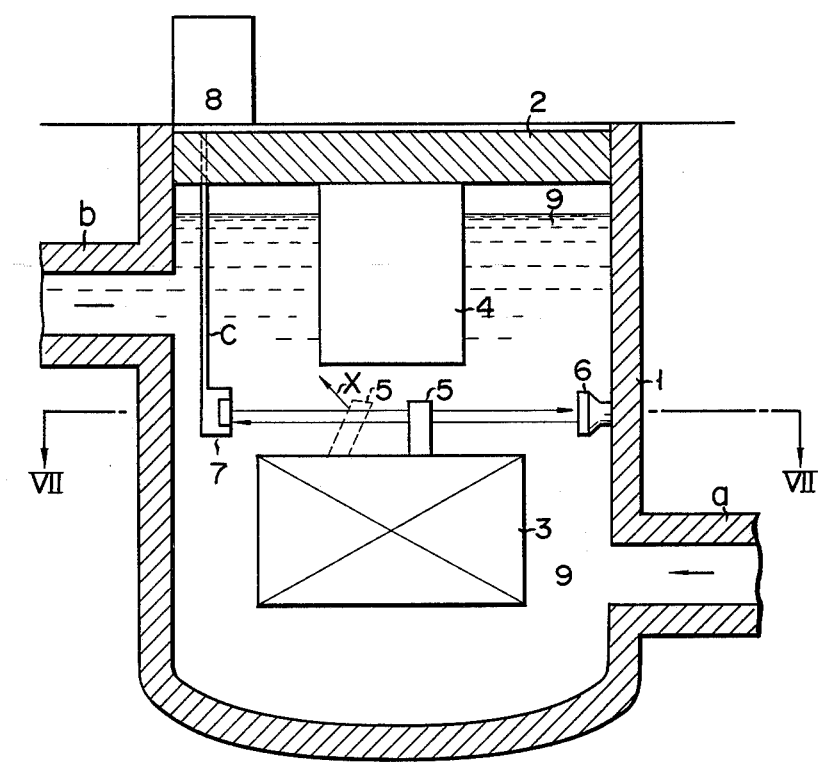
FIG. 1 is a cross sectional view of a conventional nuclear reactor.

To reiterate, the nuclear reactor shown in FIG. 7 is substantially equal to that shown in FIG. 1 except the reflective member. Namely, the nuclear reactor of this invention comprises the reactor vessel 1, the core 3 housed in the reactor vessel, the ultrasonic transducer 7 mounted in the vicinity of the upper end of the core 3 for emitting and receiving the ultrasonic wave signal, and the reflective members $6b$, $6b_1$, $6b_2$, $6b_3$, etc. mounted in a manner to face the transducer 7. Further, the nuclear reactor comrises, though not shown in the drawings, means for rotating the transducer 7 by a prescribed angle to scan horizontally the ultrasonic wave signal emitted from the transducer and means for displaying the reflected signal received by the transducer, as is the case with a conventional nuclear reactor.

The particular shape of the groove 10 of the reflective member is advantageous in that the incident ultrasonic wave is reflected twice by the walls defining the groove such that the wave leaving the groove is propagated in the direction parallel with the incident direction whatever the incident angle may be. It follows that the echo returns to the transducer without fail even if the reflective member $6b$ is mounted in an inclined fashion or the inclination is caused by deformation of the reflective member with time.

FIG. 7 shows that the reflective member $6b$ is appreciably inclined with respect to the incident direction of the ultrasonic wave signal. Namely, the member $6b$ is not perpendicular to the incident direction of the signal. It should be noted that, if it is intended to mount the reflective member perpendicular to the incident direction of the wave signal, only a slight deviation of the reflective member causes interferences among the echos coming from the plurality of grooves 10. To be more specific, the inclination angle ($\theta_o$) of the reflective member causing the echo level to become zero by interference is given by the following equation:

$$\theta_o = \sin^{-1} \frac{\lambda}{2an} \quad (1)$$

where, $\theta_o$ ... the inclination of the reflective member, i.e., the angle between the vertical plane perpendicular to the incident direction of the wave signal and the vertical plane including the edges of the two walls defining the groove of the reflective member, $\lambda$ ... the wavelength of the ultrasonic wave, a ... the length of the line joining the edges of the two walls defining the reflective member, n ... the number of grooves.

The value of $\theta_o$ is 0.2°, if $\lambda = 1.0$ mm, $a = 50$ mm and $n = 3$ are substituted in equation (1). This means that the inclination of the reflective member should not be greater than 0.2°. What should be noted is that the value of 0.2° is easily reached by inaccuracy in the step of mounting the reflective member or by thermal deformation with time of the reflective member, where the reflective member is mounted perpendicular to the incident direction of the wave signal.

Needless to say, the inclination of the reflective member should not exceed 45°. If the inclination is greater than 45°, the travelling path of the echo fails to be parallel with the incident direction of the ultrasonic wave signal. Further, the inclination angle should not be unduly close to 45° because the larger inclination results in the smaller effective reflection area of the reflective member.

The inclination of the reflective member gives rise to different distances of the grooves from the transducer. In FIG. 2, for example, the round-trip passageway of the wave signal reflected by groove $Q_1$, is longer by $2a \sin \theta$ than that of the signal reflected by the adjacent groove $Q_2$ ($\Delta l = 2a \sin \theta$). Naturally, the echoes from the grooves $Q_1$ and $Q_2$ differ from each other in phase. What should be noted is that the echo level becomes zero by interference if the difference ($\Delta l$) is unduly small. In order to prevent this difficulty, the value of ($\Delta l$) should be determined to meet the following relationship:

$$\tau < \frac{\Delta l}{c} \quad (2)$$

where, $\tau$: pulse width of the ultrasonic wave, c: speed of sound

Figure 4:
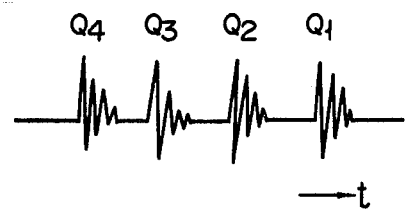
FIG. 4 shows the wave form of the echo coming from the reflective member shown in FIG. 2.

If $\Delta l$ is determined to meet the relationship (2), the echo from the reflective member $6b$ has a pulse wave form as shown in FIG. 4 and, thus, is free from interference or overlapping problem. In other words, the reflective member is inclined in order to obtain the echo of the pulse wave form as shown in FIG. 4.

Figure 5:
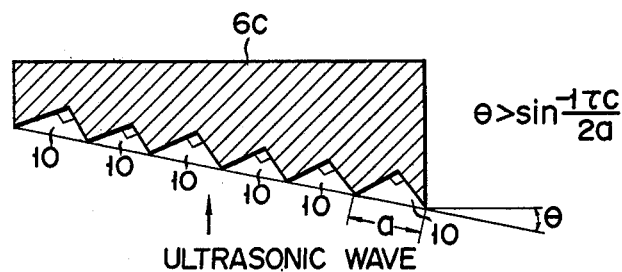
FIGS. 5 and 6 are plan views of reflective members according to additional embodiment of this invention.
Figure 6:
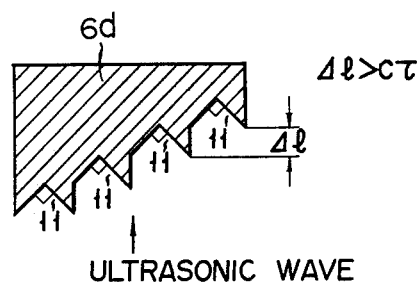

FIGS. 5 and 6 show reflective members $6c$ and $6d$, respectively, according to additional embodiments of this invention. In the embodiment of FIG. 5, grooves 10 shaped like the grooves 10 of FIG. 2 are formed in the inclined plane of the body of the reflective member $6c$. On the other hand, the reflective member $6d$ of FIG. 6 comprises grooves 11 each having a right-angled corner and an obtuse-angled corner. As in FIG. 5, the grooves 11 of FIG. 6 are formed in the inclined plane of the body of the reflective member. In order to prevent the interference of the echoes, the reflective members of FIGS. 5 and 6 should meet the conditions of $\theta > \sin^{-1} \tau c/2a$ and $\Delta l > c\tau$, respectively.

In FIG. 7, the reflective members 6b, etc. are arranged equidistantly from the the transducer 7. But, this arrangement is not limitative in this invention.

FIG. 8 shows the relationship between the inclination of the reflective member and the echo level for both cases of the present invention and the prior art. In the drawing, the solid line represents the present invention in which the values of a, $\tau$ and n are 50 mm, 5 mm and 3, respectively, with the broken line indicating the prior art. It is seen that the echo level is zero at 1.5° of inclination of the reflective member in the case of the prior art. On the other hand, the difference in echo level is very small in the case of the present invention over a wide range of the inclination angles of the reflective member. Suppose it is intended to mount the reflective member at an inclination of 10°. In this case, the difference in echo level is within the range of ±15% even if the actual inclination deviates from the aimed inclination by ±5° (compare the echo level at 10° of inclination with that at 5° or 15° of inclination).

The shapes of the reflective surface of the reflective member according to this invention need not be restricted to those shown in FIGS. 2, 5 and 6. For example, it is possible to provide the reflective member with grooves or projections semi-circular in cross section.

As described above in detail, the nuclear reactor of this invention permits markedly alleviating the accuracy in mounting the reflective member, thereby prominently facilitating the mounting and maintenance of the reflective member. Further, the nuclear reactor need not be equipped with a driving system used in the prior art for adjusting the angular position of the reflective member. This is effective for simplifying the mechanism disposed over the rotatable plug of the reactor. It is also important to note that the nuclear reactor of this invention permits shortening the time of examination by fluoroscopy.

What is claimed as new and desired to be secured by Letters Patent of the United States is:

1. A nuclear reactor, comprising a reactor vessel, a core housed in the reactor vessel, an ultrasonic transducer mounted in the vicinity of the upper end of the core for emitting and receiving an ultrasonic wave pulse signal propagating above the core, means for rotating the transducer by a prescribed angle to scan horizontally the ultrasonic wave emitted from the transducer, a plurality of reflective members mounted in the vicinity of the upper end of the core in a manner to face the transducer for reflecting the ultrasonic wave signal emitted from the transducer, means for energizing the transducer, and means for displaying the ultrasonic wave signal reflected by the reflective members and received by the transducer in synchronism with the wave scanning motion of the transducer, wherein each of the reflective members is provided with a number of reflective surfaces arranged in the scanning direction of the ultrasonic wave and shaped to permit the incident ultrasonic wave to be reflected a plurality of times such that the reflected wave returning to the transducer runs along a path parallel with and differing from the path of the incident wave, and the reflective surfaces differ from each other in distance from the transducer so as to prevent interference among the reflected ultrasonic wave signals; wherein the difference ($\Delta l$) in round trip distance from the transducer between two adjacent reflective surfaces meets the following relationship:

$$\Delta l > c\tau$$

where, c . . . speed of sound $\tau$ . . . pulse width of the ultrasonic wave.

2. The nuclear reactor of claim 1, wherein an angle $\theta$ made between the vertical plane including the edges of the reflective surfaces and the vertical plane perpendicular to the incident direction of the ultrasonic wave meets the following relationship $$\sin^{-1}\frac{\tau c}{2a} < \theta < 45°$$

where, $\tau$ . . . pulse width of the ultrasonic wave, c . . . speed of sound, and a . . . length of the line joining the edges of the reflective surfaces.

3. The nuclear reactor according to claim 2, wherein the reflective member is consecutively provided with a plurality of grooves each shaped such that two walls defining the groove cross at right angles.

4. The nuclear reactor according to claim 1, wherein the reflective member is consecutively provided with a plurality of grooves each having a right-angled corner and an obtuse-angled corner and the distances of the grooves from the transducer are different from each other by a predetermined amount.

5. The nuclear reactor according to claim 2 or 1, wherein said reflective surfaces of the reflective member are consecutively made semi-circular in cross section.

6. The nuclear reactor according to claim 5, wherein said reflective surfaces of the reflective member are consecutively provided with a plurality of grooves each shaped semi-circular in cross section.

7. The nuclear reactor according to claim 5, wherein said reflective surfaces of the reflective member are consecutively provided with a plurality of projections each shaped semi-circular in cross section.

* * * * *